(12) United States Patent
Suckow et al.

(10) Patent No.: US 9,220,770 B2
(45) Date of Patent: Dec. 29, 2015

(54) EXTRACELLULAR MATRIX MATERIALS AS VACCINE ADJUVANTS FOR DISEASES ASSOCIATED WITH INFECTIOUS PATHOGENS OR TOXINS

(75) Inventors: Mark A. Suckow, Granger, IN (US); William R. Wolter, Granger, IN (US); Paul J. Hall, Lafayette, IN (US)

(73) Assignees: The University of Notre Dame, Notre Dame, IN (US); Cook Biotech, Inc., West Lafayette, IN (US)

( * ) Notice: Subject to any disclaimer, the term of this patent is extended or adjusted under 35 U.S.C. 154(b) by 112 days.

(21) Appl. No.: 12/868,908

(22) Filed: Aug. 26, 2010

(65) Prior Publication Data

US 2011/0076305 A1    Mar. 31, 2011

Related U.S. Application Data

(63) Continuation-in-part of application No. 11/699,448, filed on Jan. 30, 2007, which is a continuation-in-part of application No. 11/583,771, filed on Oct. 20, 2006, now Pat. No. 8,778,360.

(60) Provisional application No. 60/730,379, filed on Oct. 27, 2005.

(51) Int. Cl.
 A61K 39/39    (2006.01)
 A61K 39/00    (2006.01)
 A61K 39/08    (2006.01)

(52) U.S. Cl.
 CPC ............... *A61K 39/39* (2013.01); *A61K 39/08* (2013.01); *A61K 2039/55511* (2013.01); *A61K 2039/55588* (2013.01)

(58) Field of Classification Search
 CPC .......... A61K 2039/55511; A61K 2039/55588; A61K 39/08
 See application file for complete search history.

(56) References Cited

U.S. PATENT DOCUMENTS

| 2,172,903 | A | 9/1939 | Charping |
|---|---|---|---|
| 3,346,401 | A | 10/1967 | Barat et al. |
| 3,562,820 | A | 2/1971 | Braun |
| 3,810,473 | A | 5/1974 | Cruz, Jr. et al. |
| 4,502,159 | A | 3/1985 | Woodruff et al. |
| 4,578,067 | A | 3/1986 | Cruz, Jr., et al. |
| 4,902,508 | A | 2/1990 | Badylak et al. |
| 4,956,178 | A | 9/1990 | Badylak et al. |
| 5,028,695 | A | 7/1991 | Eckmayer et al. |
| 5,275,826 | A | 1/1994 | Badylak et al. |
| 5,281,422 | A | 1/1994 | Badylak et al. |
| 5,336,616 | A | 8/1994 | Livesey et al. |
| 5,352,463 | A | 10/1994 | Badylak et al. |
| 5,437,287 | A | 8/1995 | Phillips et al. |
| 5,460,962 | A | 10/1995 | Kemp |
| 5,480,424 | A | 1/1996 | Cox |
| 5,507,810 | A | 4/1996 | Prewett et al. |
| 5,554,389 | A | 9/1996 | Badylak et al. |
| 5,733,337 | A | 3/1998 | Carr, Jr. et al. |
| 5,782,914 | A | 7/1998 | Schankerelli |
| 5,837,269 | A | 11/1998 | Daynes et al. |
| 6,156,305 | A | 12/2000 | Brauker et al. |
| 6,206,931 | B1 | 3/2001 | Cook et al. |
| 6,207,147 | B1 | 3/2001 | Hiserodt et al. |
| 6,218,166 | B1 | 4/2001 | Ravindranath et al. |
| 6,264,992 | B1 | 7/2001 | Voytik-Harbin et al. |
| 6,277,368 | B1 | 8/2001 | Hiserodt et al. |
| 6,403,104 | B1 | 6/2002 | Berd et al. |
| 6,406,689 | B1 | 6/2002 | Falkenberg et al. |
| 6,451,971 | B1 | 9/2002 | Akiyama et al. |
| 6,548,066 | B1 | 4/2003 | Michaeli et al. |
| 6,699,483 | B1 | 3/2004 | Dalgleish et al. |
| 7,015,205 | B1 | 3/2006 | Wallack et al. |
| 7,090,853 | B2 | 8/2006 | Kapp et al. |
| 7,175,652 | B2 | 2/2007 | Cook et al. |
| 7,550,004 | B2 | 6/2009 | Bahler et al. |
| 2001/0006631 | A1 | 7/2001 | Hiserodt et al. |

(Continued)

FOREIGN PATENT DOCUMENTS

| WO | 9624661 | 8/1996 |
|---|---|---|
| WO | WO 97/36495 | 10/1997 |

(Continued)

OTHER PUBLICATIONS

Badylak et al., Acta Biomaterialia, 2009, 5:1-13, available online Oct. 2, 2008.*
International Search Report for PCT/US09/35062, dated Jul. 22, 2009.
Abraham, et al., "Evaluation of the porcine intestinal collagen layer as a biomaterial". (1999) 29: 442-452.
Aguzzi, et al., "Pathogenesis of Prion Diseases: Current Status and Future Outlook", Microbiology (2006) 4: 765-775.
Aguzzi et al., (2003), "Immune system and peripheral nerves in propagation of prions to CNS," Br Med Bull., 2003;66: 141-59.
Akhurst, Rosemary, J. Clin, Invest, (2002) 109: 1533-1536.
Allman et al., (2001), "Xenogeneic extracellular matrix grafts elicit a TH2-restricted immune response," Transplantation, 71:1631-1640.
Arbel et al., (2003), "Generation of antibodies against prion protein in wild-type mice via helix 1 peptide immunization," J Neuroimmunol., 144(1-2):38-45.

(Continued)

*Primary Examiner* — Stacy B Chen
(74) *Attorney, Agent, or Firm* — Husch Blackwell LLP; Denise L. Mayfield

(57) ABSTRACT

Disclosed are vaccines and vaccine adjuvants useful in the treatment and/or prevention of infection and diseases associated with infectious pathogens, such as tetanus, as well as diseases associated with biological toxins. Also provided are methods of preparing an adjuvant and the vaccine containing the adjuvant. Methods are also provided for vaccinating/immunizing an animal against infection and diseases associated with infectious pathogens, such as tetanus, and other diseases associated with biological toxins. Adjuvant materials are presented that are prepared from an extracellular matrix material. The adjuvant may also be described as a heterologous acellular collagenous tissue preparation. The adjuvants are demonstrated to enhance the immunogencity of an infectious pathogen antigen or biological toxin antigen of interest, as well as to enhance the survival of an immunized animal.

16 Claims, 6 Drawing Sheets

(56) References Cited

U.S. PATENT DOCUMENTS

| | | | |
|---|---|---|---|
| 2004/0013712 | A1 | 1/2004 | Parma |
| 2006/0099675 | A1 | 5/2006 | Bernard |
| 2006/0265053 | A1 | 11/2006 | Hunt |
| 2009/0248144 | A1 | 10/2009 | Bahler et al. |

FOREIGN PATENT DOCUMENTS

| | | | |
|---|---|---|---|
| WO | WO 03/017745 | A2 * | 3/2003 |
| WO | WO 03/100034 | | 12/2003 |

OTHER PUBLICATIONS

Badylak, S.F., Small Intestinal Submucosa (SIS); A Biomaterial Conducive to Smart Tissue Remodeling, Tissue Engineering; Current Perspectives, Bell E (ed). Burkhauser Publishers, Cambridge, MA., (1993), pp. 179-189.

Badylak, S.F., "The Extracellular Matrix as a Scaffold for Tissue Reconstruction", Seminars in Cellular and Developmental Biology, (2002); 13:377-383.

Badylak, S.F., et al., J. Surg. Res., (1989) 47: 74-80.

Badylak SF, et al.., Journal of Biomaterials Sciences Polymer Edition, (1998) 9(8): 863-878.

Banzhoff et al., (2003), "A new MF59-adjuvanted influenza vaccine enhances the immune response in the elderly with chronic diseases: results from an immunogenicity meta-analysis," Gerontology, 49(3):177-84.

Barr, TA, et al., "Co-stimulatory agonists as immunological adjuvants". Vaccine, (2006) 24: 3339-3407.

Baars et al., (2000), "Skin tests predict survival after autologous tumor cell vaccination in metastatic melanoma: experience in 81 patients," Ann. Oncol., 11:965-970.

Bello-Deocampo D, et al., "TGF-beta/Smad signaling in Prostate Cancer", Curr. Drug Targets, (2003) 4: 197-207.

Ben-Efraim et al., (2000), "Use of xenogenized (modified) tumor cells for treatment in experimental tumor and in human neoplasia," Biomed & Pharmacotherapy, 54:268-273.

Benbow M., "Oasis: An Innovative Alternative Dressing for Chronic Wounds", Br. J. Nurs, (2001) 10(22): 1489-1492.

Bendandi, M, et al., Leuk. Lymphoma., (2006) 47(1): 29-37.

Berd D, et al., J. Clin Oncol., (1997) 15: 2359-2370.

Berd et al., (1990), "Treatment of metastatic melanoma with an autologous tumor-cell vaccine: clinical and immunologic results in 64 patients," J. Clin. Oncol., 8:8158-1867.

Bergman, Phillip J. et al., "Long-Term Survival of Dogs with Advanced Malignant Melanoma After DNA Vaccination with Xenogenetic Human Tyrosinase: A Phase I Trial," Clinical Cancer Research, Apr. 2003, 9: 1284-1290.

Berraondo et al., (2007), "Eradication of large tumors in mice by a tritherapy targeting the innate, adaptive, and regulatory components of the immune system," Cancer Res., 67:8847-8855.

Bissell MJ. et al., J. Cell Sci. Suppt., (1987) 8: 327-343.

Bodey et al., (2000), "Failure of cancer vaccines: the significant limitations of this approach to immunotherapy," Anticancer Res., 20:2665-2676.

Boring, CC, et al., "Cancer Statistics" CA Cancer Journal for Clinicians, 1993, 43: 7-26.

Brando et al., (2007), "Murine immune responses to liver-stage antigen 1 protein FMP011, a malaria vaccine candidate, delivered with adjuvant AS01B or AS02A," Infect Immun., 75(2):838-45.

Brewer J.M., "How do Aluminum Adjuvants Work?" Immunol Lett., (2006) 102: 10-15.

Brooks, et al., "Plasma Selenium Level Before Diagnosis and the Risk of Prostate Cancer Development", Journal of Urology, Dec. 2001, 166: 2034-3038.

Brown-Etris M, Cutshall WD, Hiles M.C., Wounds, (2002) 14(4): 150-166.

Burch et al., (2000), "Priming tissue-specific cellular immunity in a phase I trial of autologous dendritic cells for prostate cancer," Clin. Cancer Res., 6:2175-2182.

Burch et al., (2004), "Immunotherapy (APC8015, Provenge) targeting prostatic acid phosphatase can induce durable remission of metastatic androgen-independent prostate cancer: a phase 2 trial," Prostate, 60:197-204.

Caglar et al., (2005), "Effect of monophosphoryl lipid A on antibody response to diphtheria toxin and its subunits," APMIS, 113(4):256-63.

Caughey, et al., "Prions and their Partners in Crime", Nature, (2006) 44: 803-810.

Chang et al., (2000), "Antigen-Specific Cancer Immunotherapy Using a GM-CSF secreting allogeneic tumor cell-based vaccine," Int. J. Cancer, 86:725-730.

Chatterjee et al., (1994), "Idiotypic antibody immunotherapy of cancer," Cancer Immunol. Immunother., 38:75-82.

Charles, Linda G., et al., "Antitumor Efficacy of Tumor-Antigen-Encoding Recombinant Poxvirus Immunization in Dunning Rat Prostate Cancer: Implicatios for Clinical Genetic Vaccine Development." World J. Urolo., (2000) 18: 136-142.

Corman et al., (1998), "Recognition of prostate-specific antigenic peptide determinants by human CD4 and CD8 T cells," Clin. Exp. Immunol., 114:166-172.

Correale et al., (1997), "In vitro generation of human cytotoxic T lymphocytes specific for peptides derived from prostate-specific antigen," J. Natl. Cancer Inst. USA, 89:293-300.

Culora GA, et al., "Aluminum and Injection Site Reactions" J. Clin. Pathol., (1996) 49: 844-847.

Cunha, Gerald R. "Role of the Stromal Microenvironment in Carcinogenesis of the Prostate," Int. J. Cancer, (2003) 107: 1-10.

De Souza Matos et al., (2000), "Immunostimulatory effects of polar glycopeptidolipids of *Mycobacterium chelonae* for inactivated rabies vaccine," Vaccine, 18(20):2125-31.

Degruijl et al., (1999), "Cancer vaccine strategies get bigger and bigger," Nature Medicine, 5:1124-1125.

Denmeade et al., (2003), "Prostate specific antigen (PSA) does not affect growth of prostate cancer cells in vitro or prostate cancer xenografts in vivo," Prostate, 56:45-53.

Desai et al., (2000), "Immune response with biodegradable nanospheres and alum: studies in rabbits using staphylococcal enterotoxin B-toxoid," J Microencapsul., 17(2):215-25.

Dillman et al., (1998), "Clinical experience with autologous tumor cell lines for patient-specific vaccine therapy in metastatic melanoma," Cancer Biother. Radiopharm., 13:165-173.

Dillman et al., (2001), "Short-term cell lines from breast cancer for use as autologous tumor cell vaccines in the treatment of breast cancer," Cancer Biotherapy & Radiopharmaceuticals, 16:205-211.

Dols et al., (2003), "Vaccination of women with metastatic breast cancer using a costimulatory gene (CD80)-modified, HLA-A2 matched allogeneic, breast cancer cell line: clinical and immunological results," Human Gene Therapy, 14:1117-1123.

Donnelly, (2003), "Cancer vaccine targets leukemia," Nature Medicine, 9:1354-1356.

Eaton et al., (2002), "Allogeneic whole-cell vaccine: a phase I/II study in men with hormone-refractory prostate cancer," British Journal of Urology, 89:19-26.

Edwards B.K. et al., J Nat'l Cancer Inst (2005) 97(19): 1407-1427.

Eldridge et al., (1991), "Biodegradable and biocompatible poly(DL-lactide-co-glycolide) microspheres as an adjuvant for staphylococcal enterotoxin B toxoid which enhances the level of toxin-neutralizing antibodies," Infect Immun., 59(9):2978-86.

Enari et al., (2001), "Scrapie prion protein accumulation by scrapie-infected neuroblastoma cells abrogated by exposure to a prion protein antibody," Proc Natl Acad Sci U S A, 98(16):9295-9.

Evans et al., (1999), "Vaccine therapy for cancer—fact or fiction?" Q. J. Med., 92:299-307.

Ezzell, (1995), "Cancer 'vaccines': an idea whose time has come?" J. NIH Res., 7:4-49.

Fernandez-Acenero, M.J. et al., "Prognosis Influence of Tumor-Associated Eosinophilic Infiltrate in Colorectal Cancinoma," Cancer, (2002) 88: 1544-1548.

Finn et al., (2002), "Prophylactic Cancer Vaccines," Curr. Opin. Immunol., 14:172-177.

(56) References Cited

OTHER PUBLICATIONS

Flick-Smith et al., (2002), "Mucosal or parenteral administration of microsphere-associated Bacillus anthracis protective antigen protects against anthrax infection in mice," Infect Immun., 70(4):2022-8.
Forni et al., (2000), "Immunoprevention of cancer," Cancer Res., 60:2571-2575.
Fong, Lawrence et al., "Dendritic Cell-Based Xenoantigen Vaccination or Prostate Cancer Immunotherapy," The Journal of Immunology, (2001) 167: 7150-7156.
Frost et al., (1975), "Tumor immunoprophylaxis in mice using glutaraldehyde-treated syngenic tumor cells," Cancer Res., 35:2646-2650.
Fuessel et al., (2006), "Vaccination with hormone-refractory prostate cancer patients with peptide cocktail-loaded dendritic cells: results of phase I clinical trial," Prostate, 66:811-821.
Fukino K, et al., Cancer Res. (2004) 64: 7231-7236.
Furbert-Harris, Paulette et al., "Inhibition of Prostate Cancer Cell Growth by Activated Eosinophils" Prostate, (2003) 57: 165-175.
Gann, et al., "Lower Prostate Cancer Risk in Men with Elevated Plasma Lycopene Levels: Results of a Prospective Analysis", JAMA, May 12, 1999, 281(18): 1682.
Gann, et al., "Lower Prostate Cancer Risk in Men with Elevated Plasma Lycopene Levels: Results of a prospective Analysis", Cancer Research, Mar. 15, 1999, vol. 59, pp. 1225-1230.
Gikh et al., (2003), "Polyclonal anti-PrP auto-antibodies induced with dimeric PrP interfere efficiently with PrPSc propagation in prion-infected cells," J Biol Chem., 278(20): 18524-31.
Glenn GM, Kenney R.R., Curr. Topics Microbiol. Immunol., (2006) 304: 247-268.
Granziero et al., (1999), "Adoptive immunotherapy prevents prostate cancer in a transgenic animal model," Eur. J. Immunol., 29:1127-1138.
Greenlee RT, et al., "Cancer Statistics", (2001), CA Cancer J Clin. (2001) 51: 15-36.
Griffiths et al., (1997), "Liposomally-encapsulated ricin toxoid vaccine delivered intratracheally elicits a good immune response and protects against a lethal pulmonary dose of ricin toxin," Vaccine, 15(17-18):1933-9.
Griffith, Thomas S., et al., "Inhibition of Murine Prostate Tumor Growth and Activation of Immunoregulatory Cells with Recombinant Canarypox Viruses." Journal of the National Cancer Institute, Jul. 4, 2001, vol. 93, No. 13, pp. 998-1007.
Gu et al., (2002), "Substitution of porcine small intestinal submucosa for rabbit Achilles tendon, an experimental study," Natl. Med. J. China, 82:1279-1282 (Chinese language with English abstract).
Gulley, et al., "Phase I Study of a Vaccine Using Recombinant Vaccinia Virus Expressing PSA (rV-PSA) in Patients with Metastatic Androgen-Independent Prostate Cancer", The Prostate, 2002, vol. 53, pp. 109-117.
Hahn et al., (2006), "Short-term dietary administration of celecoxib enhances the efficacy of tumor lysate-pulsed dendritic cell vaccines in treating murine breast cancer," Int. J. Cancer, 118:2220-2231.
Hanan et al., (2001), "Antiaggregating antibody raised against human PrP 106-126 recognizes pathological and normal isoforms of the whole prion protein," Cell Mol Neurobiol., 21(6):693-703.
Hanan et al., (2001), "Immunomodulation of the human prion peptide 106-126 aggregation," Biochem Biophys Res Commun., 280(1):115-20.
Harada et al., (2003), "Prostate-specific antigen-derived epitopes capable of inducing cellular humoral responses in HLA-A24+ prostate cancer patients," Prostate, 57:152-159.
He, Qiu-ming et al., "Inhibition of tumor Growth with a Vaccine based on Xenogensic Homologous Fibroblast Growth Factor Receptor-1 in Mice," Journal of Biological Chemistry, Jun. 13, 2003, vol. 24, pp. 21831-21836.
He, Xianghui, et al., "Antigen epitope-expressing cytokines for DNA immunization" Vaccine, (2005) 23: 1966-1972.
Hedlund et al., (2001), "Negligible adjuvant effect for antibody responses and frequent adverse events associated with IL-12 treatment in humans vaccinated with pneumococcal polysaccharide," Vaccine, 20(1-2):164-9.
Higaki, et al., "Collagen minipellet as a controlled release delivery system for tetanus and diptheria toxoid", (2001) 19: 3091-3096.
Higgins et al., (1996), "MF59 adjuvant enhances the immunogenicity of influenza vaccine in both young and old mice," Vaccine, 14(6):478-84.
Hodde, et al., "Small Intestinal Submucosa Does Not Promote PAIII Tumor Growth in Lobund-Wistar Rats", (2004) 120: 189-194.
Hodde, et al., "Virus Safety of a Porcine-Derived Medical Device: Evaluation of a Viral Inactiviation Method" Biotechnol. Bioeng., (2002) 79: 211-216.
Hodde, JP., et al., J. Surg. Res., (2004); 120: 189-194.
Hodge, et al. "Costimulatory Molecules as Adjuvants for Immunotherapy", Frotiers in Bioscience, (2006) 11: 788-803.
Horiguchi et al., (2002), "Screening of HLA-A24-restricted epitope peptides from prostate-specific membrane antigen that induces specific antitumor cytotoxic T lymphocytes," Clin. Cancer Res., 8:3885-3892.
Hrouda, et al., "*Mycobacterium vaccae* (SRL172): a Potential Immunological Adjuvant Lelevated in Rat Prostate Cancer", British Journal of Urology, (1998) 82: 870-876.
Hrouda, et al., "Allogenic Whole-Tumor Cell Vaccination in the Rat Model of Prostate Cancer in Man", BJU International (2002) 89: 19-26.
Huang, C.M., et al., Proteomics, (2005) 5: 1013-1023.
Hursting, et al., "Types of Dietary Fat and the Incidence of Cancer at Five Sites," Preventative Medicine, (1990) 19: 242-253.
Jaganathan et al., (2006), "Strong systemic and mucosal immune responses to surface-modified PLGA microspheres containing recombinant hepatitis B antigen administered intranasally," Vaccine, 24(19):4201-11.
Jager et al., (2003), "Antigen-specific immunotherapy and cancer vaccines," Intl. J. Cancer, 106:817-820.
Jarvinen et al., (2000), "Intranasal vaccination of New Zealand white rabbits against pasteurellosis using alginate-encapsulated Pasteurella multocida toxin and potassium thiocyanate extract," Comparative Medicine, 50:263-269.
Jocham et al., (2004), "Adjuvant autologous renal tumour cell vaccine and risk of tumour progression in patients with renal-cell carcinoma after radical neprectomy: phase III, randomised controlled trial," Lancet, 363:594-599.
Kenney, R.T., et al., J. Infect. Dis., (2004) 190: 775-782.
Kende et al., (2006), "Enhancement of intranasal vaccination in mice with deglycosylated chain A ricin by LTR72, a novel mucosal adjuvant," Vaccine, 15;24(12):2213-21.
Kenney et al., (1999), "Protective immunity using recombinant human IL-12 and alum as adjuvants in a primate model of cutaneous leishmaniasis," J Immunol., 163(8):4481-8.
Kobayashi et al., (2003), "Identification of naturally processed helper T-cell epitopes from prostate-specific membrane antigen using peptide-based in vitro stimulation," Clin. Cancer Res., 9:5386-5393.
Kochenderfer et al., (2007), "Maximizing CD8+ T cell responses elicited by peptide vaccines containing CpG oligodeoxynucleotides," Clin. Immunol., 124:119-130.
Koller et al., (2002), "Induction of antibodies against murine full-length prion protein in wild-type mice," J Neuroimmunol., I32(1-2):113-6.
Komenaka et al., (2004), "Immunotherapy for melanoma," Clinics in Dermatology, 22:251-265.
Knoll L.D., *Urology*, (2002) 59(5): 758-761.
Knoll L.D., *Urology*, (2001) 57(4) 753-767.
Langermans et al., (2005), "Effect of adjuvant on reactogenicity and long-term immunogenicity of the malaria Vaccine ICC-1132 in macaques," Vaccine, 23(41):4935-43.
Lantz, G.C., et. al., "Small Intestinal Submucosa as a Vascular Graft: a Review". J. Invest. Surg., (1993) (6) 297-310.
Lantz, G.C., et al., "Small Intestinal Submucosa as a Small-Diameter Arterial Graft in the Dog". J. Invest. Surg., (1990) (3) 217-227.

(56) References Cited

OTHER PUBLICATIONS

Lee et al., (1999), "Increased vaccine-specific T cell frequency after peptide-based vaccination correlates with increased susceptibility to in vitro stimulation but does not lead to tumor regression," J. Immunol., 163:6292-6300.
Levesque et al., (2006), "Association between immunogenicity and adsorption of a recombinant *Streptococcus pneumoniae* vaccine antigen by an aluminum adjuvant," Hum Vaccin., 2(2):74-7.
Lindblad, "Aluminum compunds for use in vaccines." Immunology and Cell Biology (2004) 82: 497-505.
Lord et al., (2007), "Low dose metronomic oral cyclophosphamide for hormone resistant prostate cancer: a phase II study," J. Urology, 177:2136-2140.
Lu et al., (2002), "Rcognition of prostate tumor cells by cytotoxic T lymphocytes specific for prostate-specific membrane antigen," Cancer Res., 62:5807-5812.
Lubaroff et al., (2006), "Decreased cytotoxic T cell activity generated by co-administration of PSA vaccine and CpG ODN is associated with increased tumor protection in a mouse model of prostate cancer," Vaccine, 24:6155-6162.
Mantovani F., et al., Eur Urol., (2003) 44: 600-602.
Martin, (1997), "Development of an adjuvant to enhance the immune response to influenza vaccine in the elderly," Biologicals, 25(2):209-131.
Matrisian LM, et al., Cancer Res., (2001) 61(9): 3844-3846.
Matsueda et al., (2005), "Identification of peptide vaccine candidates for prostate cancer patients with HLS-A3 super-type alleles," Clin. Cancer Res., 11:6933-6943.
McDevitt CA, et al., J. Biomed. Mater. Res., (2003) 67A: 637-646.
McNeel et al., (2001), "Identification of T helper epitopes from prostatic acid phosphatae," Cancer Res., 61:5161-5167.
Mendez et al., (2003), "Coinjection with CpG-containing immunostimulatory oligodeoxynucleotides reduces the pathogenicity of a live vaccine against cutaneous Leishmaniasis but maintains its potency and durability," Infect Immun. 71(9):5121-9.
Michael, Agniesla, et al., "Delayed Disease Progression after Allogenic Cel Vaccination in Mormone-Resistant Prostate Cancer and Correlation with Immunologic Variables." Clin. Cancer Res., Jun. 15, 2005, 11(12) 469-478.
Miller et al., (2006), "The role of melatonin in immuno-enhancement: potential application in cancer," Int. J. Exp. Path., 87:81-87.
Moody et al., (1994), "Interleukin-2 transfected prostate cancer cells generate a local antitumor effect in vivo," Prostate, 24:244-251.
Moschella F, et al., Onco res., (2003) 14(3): 133-145.
Mosolits S., et al., "Towards Therapeutic Vaccines for Colorectal Carcinoma: A Review of Clinical Trials" Expert Rev. Vaccines, (2005) 4(3): 329-350.
Mullen et al., (2006), "Enhancement of functional antibody responses to AMA1-C1/Alhydrogel, a Plasmodium falciparum malaria vaccine, with CpG oligodeoxynucleotide," Vaccine, 24(14):2497-505.
Nomura, et al., "Serum Selenium and Subsequent Risk of Prostate Cancer", Cancer Epidemiology, Biomarker & Prevention, Sep. 2000, 9: 883-887.
O'Connor R.C., et al., Urology, (2002) 60: 697x-697xii.
O'Connor R.C., et al., Urology, (2002) 60: 906-909.
O'Connor R.C., et al., Journ. of Urology, (2001) 165: 1995.
Ochsenbein et al., (1999), "Immune surveillance against a solid tumor fails because of immunological ignorance," Proc. Natl. Acad. Sci. USA, 96:2233-2238.
Ohashi, Yusuke et al., "Significance of Tumor Associated tissue Eosinophilia and Other Inflamatory Cell Infiltrate in Early Esophageal Squamous Cell Carcinoma," Anticancer Research, (2002) 20: 3025-33030.
Okaji et al., (2004), "Vaccination with autologous endothelium inhibits angiogenesis and metastasis of colon cancer through autoimmunity," Cancer Science, 95:85-90.
Palese, (2006), "Making better influenza virus vaccines?" Emerg Infect Dis., 12(1):61-5.
Paradiso M, et. al., Arch Ital Urol. Androl., (2003) 75(2): 116-118.

Petrovsky N., Vaccine, (2006) 24 Suppl. 2: S2/26-S2/29.
Peng et al., (2006), "Novel vaccines for the treatment of chronic HBV infection based on mycobacterial heat shock protein 70," Vaccin, 24(7):887-96.
Peretz et al., (2001), "Antibodies inhibit prion propagation and clear cell cultures of prion infectivity," Nature, 412(6848):739-43.
Petrik et al., (2007), "Aluminum adjuvant linked to Gulf War illness induces motor neuron death in mice," Neuromolecular Med., 9:83-100.
Peters et al., (1979), "Preparation of immunotherapeutic autologous tumor cell vaccines from solid tumors," Cancer Res., 39:1353-1360.
Pilla L, et al., Cancer Immunol Immunother., (2006) 55: 958-968.
Pimenta et al., (2006), "Intranasal immunization with the cholera toxin B subunit-pneumococcal surface antigen A fusion protein induces protection against colonization with *Streptococcus pneumoniae* and has negligible impact on the nasopharyngeal and oral microbiota of mice," Infect Immun., 74(8):4939-44.
Pollard et al., (2006), "Dietary prevention of hormone refractory prostate cancer in Lobund-Wistar rats: a review of studies in relevant animal model," Compo Med., 56:461-467.
Pollard, et al. "Transplantable Metastasizing Prostate Adenocarcinomas in Rats", Journal of the National Cancer Institute, Mar. 1975, 54(3): 109-117.
Pollard, et al., "Production of Autochthonous Prostate Cancer in Lobund-Wistar rats by treatments with N-Ntroso-Nmethylurea and Testosterone", JNCI, Aug. 1986, 77(2): 583-587.
Pollard, et al., "Autochthonous Prostate Adenocarcinomas in Lobund-Wistar Rats; A model System", The Prostate, 1987, 11: 219-227.
Pollard, "Lobund-Wistar Rat Model of Prostate Cancer in Man", The Prostate, (1998) 37: 1-4.
Pollard M. Suckow M.A., "Hormone-Refractory Prostrate Cancer in the Lobund-Wistar Rat", Experimental Biology and Medicine, (2005) 230: 520-526.
Pollard M, Luckert P.H., J. Natl. Cancer Inst., (1975) 54: 643-649.
Polymenidou et al., (2004), "Humoral immune response to native eukaryotic prion protein correlates with anti-prion protection," Proc Natl Acad Sci U S A,101 Suppl 2:14670-6.
Qin et al., (2004), "CpG ODN enhances immunization effects of hepatitis B vaccine in aged mice," Cell Mol Immunol., 1(2):148-52.
Rechsteiner G, et al., J. Immunol., (2005) 174: 2476-2480.
Redfern C.H., et al. J Clin Oncol., (2006) 24: 3107-3112.
Ringler, et al., "Protection of Rabbits against experimental Pasteurellosis by vaccination with a patassium Thiocynate Extract of Pastuerella multocida", Ifection and Immunity, Sep. 1985, 49(3): 498-504.
Rosado-Vallado et al., (2005), "Aluminium phosphate potentiates the efficacy of DNA vaccines against Leishmania mexicana," Vaccine, 23(46-47):5372-9.
Rosset et al., (2004), "Breaking immune tolerance to the prion protein using prion protein peptides plus oligodeoxynucleotide-CpG in mice," J Immunol., 172(9):5168-74.
Rousseauu RF, et al., Blood, (2006);107:1332-1341.
Ruozi, et al., "Intact collagen and atelocollagen sponges: Characterization and ESEM observation, Materials Science and Engineering" (2007) 27: 802-810.
Sabirov et al., (2006), "Intranasal vaccination of neonatal mice with polysaccharide conjugate vaccine for protection against pneumococcal otitis media," Vaccine, 24(27-28):5584-92.
Sanderson et al., (1974), "The induction of tumour immunity in mice using glutaraldehyde-treated tumor cells," Nature, 248:690-691.
Schultz DJ, et al., J. Am. Coll. Surg., (2002) 194: 541-543.
Schwarz et al., (2004), "Immunisation with a synthetic prion protein-derived peptide prolongs survival times of mice orally exposed to the scrapie agent," Neurosci Lett., 350(3):187-9.
Segura-Velazquez et al., (2006), "A novel synthetic adjuvant effectively enhances the immunogenicity of the influenza vaccine," Vaccine, 24(8):1073-80.
Sen et al., (2006), "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," Infect Immun., 74(4):2177-86.

(56) References Cited

OTHER PUBLICATIONS

Shekhar, Malathy et al., "Breast Stroma Plays a Dominant Regulatory Role in Breast Epithelial Growth and Differentiation: Implications for Tumor Development and Progression," Cancer Research, (2001) 61: 1320-1326.
Sigurdsson et al., (2002), "Immunization delays the onset of prion disease in mice," Am J Pathol., 161(1):13-7.
Simons J.W., Sacks N., Urol. Oncol., (2006) 24: 419-424.
Simons et al., (1999), "Induction of immunity to prostate cancer antigens: results of a clnical trial of vaccination with irradiated autologous prostate tumor cells engineered to secrete granulocyte-macrophage colony-stimulating factor using ex vivo gene transfer," Cancer Res., 59:5160-5168.
Simons et al., (2002), "Phase II trials of a GM-CSF genetransduced prostate cancer cell line vaccine (GVAX) in hormone refractory prostate cancer," Proc. Am. Soc. Clin. Oncol., 21:183a (Abstract 729).
Singh et al., (1992), "Stroma is critical for preventing or permitting immunological destruction of antigenic cancer cells," J. Exp. Med., 175:139-146.
Skountzou I, et al., Vaccine, (2006) 24: 6110-6119.
Small et al., (2000), "Immunotherapy of hormone-refractory prostate cancer with antigen-loaded dendritic cells," J. Clin. Oncol., 18:3894-3903.
Small et al., (2005), "Results of a placebo-controlled phase III trial of immunotherapy with APC8015 for patients with homrone refractory prostate cancer (HRPC)," Proc. Am. Soc. Clin. Oncol., 23(16S):378S (Abstract 4500).
Souan et al., (2001), "Modulation of proteinase-K resistant prion protein by prion peptide immunization," Eur J Immunol., 31(8):2338-46.
Srinivasan, Roopa et al., "Tumor antigens for Cancer Immunotherapy: Therapeutic Poential of Xenogeneic DNA Vaccines," Journal of Translational Medicine, 2004, vol. 2, pp. 1-12.
Stack et al., (1982), "Autologous X-irradiated tumor cells and percutaneous BCG in operable lung cancer," Thorax, 37:599-593.
Stewart et al., (2006), "Pre-clinical evaluation of new adjuvant formulations to improve the immunogenicity of the malaria vaccine RTS,S/AS02A," Vaccine, 24(42-43):6483-92.
Suckow et al., (2007), "Prevention of human PC-346C prostate cancer growth in mice by xenogeneic tissue vaccine," Cancer Immunol. Immunother., 56:1275-1283.
Suckow et al., (2007), "Surgical Repair of Experimental Achilles Tenotomy with Porcine renal capsule material in a rat model," J. Mater. Sci. Mater. Med., 18:1105-1110.
Suckow et al., (2007), "Tissue vaccines for cancer," Expert. Rev. Vacc., 6:925-937.
Suckow M.A., et al, Journal of Investigative Surgery, (1999);12:277:287.
Suckow, et al., "Heat-Labile Toxin-Producing Isolates of Pasteurella multocida from Rabbits", Laboratory Animal Science, (1991) 41(2): 151-156.
Suckow M.A., et al., J. Wound Care, (2005) 14: 137-140.
Suckow M.A., et al., "Surgical Repair of Experimental Achilles Tenotomy with Porcine Renal Capsule Material in a Rat Model" J. Mater Sci. Mater. Med., (2007) 18(6) 1105-1110.
Suckow M.A., et al., Cancer Immunology and Immunotherapy, (2005) 54: 571-576.
Sugai et al., (2005), "A CpG-containing oligodeoxynucleotide as an efficient adjuvant counterbalancing the Th1/Th2 immune response in diphtheria-tetanus-pertussis vaccine," Vaccine, 23(46-47):5450-6.
Süli et al., (2004), "Experimental squalene adjuvant. I. Preparation and testing of its effectiveness," Vaccine, 22(25-26):3464-9.
Sung et al., (2006), "HBV-ISS (Dynavax)," Curr Opin Mol Ther., 8(2):150-5.
Tatenhorst L, et al., "Genes Associated with Fast Glioma Cell Migration in vitro and in vivo" (2005);15(1 ):46-54.
Teir et al., (1957), "Effects of intraperitoneally injected suspension of roetgen irradiated and non-irradiated tumor tissue on the growth of homologous tissue," Acta Pathol. Microbiol. Scand., 40:273-282.
Theeten et al., (2005), "Effects of lowering the aluminium content of a dTpa vaccine on its immunogenicity and reactogenicity when given as a booster to adolescents," Vaccine, 10;23(12):1515-21.
Tjoe, et al., "Follow-Up Evaluation of a Phase II Prostate Cancer Vaccine Trial", The Prostate, (1999) 40: 125-129.
Tjoe, et al., "Development of a Dendritic-Cell based Prostate Cancer Vaccine", Immunology Letters, (2000) 74: 873-893.
Totterman T.H., et al., BJU Int., (2005) 96: 728-735.
Vermorken et al., (1999), "Active specific immunotherapy for stage II and stage III human colon cancer: a randomized trial," Lancet, 353:345-350.
Vieweg et al., (1994), "Immunotherapy of prostate cancer in the Dunning rat model: use of cytokine gene modified tumor vaccines," Cancer Res., 54:1760-1765.
Vitetta et al., (2006), "A pilot clinical trial of a recombinant ricin vaccine in normal humans," Proc Natl Acad Sci U S A, 103(7):2268-73.
Voytik-Harbin S.L., et al., Tissue Eng., (1998) 4: 157-174.
Wang, Z., et al., "Lack of HLA Class I Antigen Expression by Melanoma Cells SK-Mel-33 Caused by Reading a Frameshift in β2-Microglobulin Messenger RNA." J. Clin. Invest., Feb. 1993, 91: 648-692.
Wei, You-Quan, "Immunotherapy of tumors with Vaccines based on Xenogeneic Homologous Molecules," Anticancer Drugs, (2002) 13: 119-235.
Wei , Yangzhang, et al., Int. J. Oncol., (2006) 28: 585-593.
Weiser AC, et al., J. Urol, (2003) 170: 1593-1595.
Wilson et al., (1997), "Human prostate tumor angiogenesis in nude mice: metalloprotease and plasminogen activator activities during tumor growth and neovascularization of subcutaneously injected matrigel impregnated with human prostate tumor cells," Anatomical Record, 249:63-73.
Xue et al., (1997), "Induction of human cytotoxic T lymphocytes specific for prostate-specific antigen," Prostate, 30:73-78.
Zhang et al., (2003), "Dendritic cells transfected with interleukin-12 and pulsed with tumor extract inhibit growth of murine prostatic carcinoma in vivo," Prostate, 55:292-298.
Written Opinion for International Application No. PCT/US2007/081962 dated Apr. 20, 2009.
International Search Report for International Application No. PCT/US2007/081962 dated Jun. 26, 2008.
Nakaoka et al., Potentiality of gelatin microsphere as immunological adjuvant, Vaccine, 1995, pp. 653-661, vol. 13, No. 7, Elsevier Science, Ltd., Great Britain.
Eric V. Wong, "Cells:Molecules and Mechanisms", Axolotl Academic Publishing Company, (2009), Chapter 13, pp. 198-216.
Pengfei Lu et al., "Extracellular Matrix Degradation and Remodeling in Development and Disease", Cold Spring Harbor Perspectives in Biology, (2011), pp. 1-24.
Christian Frantz et al., "The Extracellular Matrix at a Glance", Journal of Cell Science 123(24), (2010), pp. 4195-4200.
Pengfei Lu et al., "The Extracellular Matrix: A Dynamic Niche in Cancer Progression", J. Cell Biology vol. 196 No. 4, Feb. 20, 2012, pp. 395-406.

* cited by examiner

EXTRACELLULAR MATRIX MATERIALS AS VACCINE ADJUVANTS FOR DISEASES ASSOCIATED WITH INFECTIOUS PATHOGENS OR TOXINS

CROSS-REFERENCE TO RELATED APPLICATIONS

This application is a continuation-in-part of U.S. patent application Ser. No. 11/699,448, filed Jan. 30, 2007, which is a continuation-in-part of U.S. patent application Ser. No. 11/583,771, filed Oct. 20, 2006, which claims priority to and the benefit of U.S. Provisional Patent Application No. 60/730,379, filed Oct. 27, 2005. The entire disclosure and contents of each of the above applications are hereby incorporated by reference.

STATEMENT OF JOINT RESEARCH AGREEMENT

In compliance with 37 C.F.R. §1.71(g)(1), disclosure is herein made that the claimed invention was made pursuant to a Joint Research Agreement as defined in 35 U.S.C. §103(c)(3), that was in effect on or before the date the claimed invention was made, and as a result of activities undertaken within the scope of the Joint Research Agreement, by or on the behalf of the University of Notre Dame and Cook Biotech, Inc. (West Lafayette, Ind.).

BACKGROUND

1. Field of the Invention

The present invention relates generally to vaccines that include an adjuvant, and to adjuvants alone. In particular, the invention relates to adjuvants derived or obtained at least in part from biological tissues, such as extracellular matrix material. In particular, the extracellular matrix material may be further described as comprising a heterologous acellular collagenous preparation, particularly a mammalian tissue preparation having these characteristics. The invention also relates to the field of methods for immunizing an animal against diseases associated with infectious pathogens, and infections by said pathogens, or toxins using a vaccine preparation that comprises includes an adjuvant comprising a heterologous acellular tissue preparation. The invention also relates to the field of methods for preparing adjuvants comprising a heterologous acellular tissue preparation, as a method for preparing an adjuvant comprising a heterologous acellular tissue preparation from a mammalian tissue so as to have these characterisitics, for use as a part of a vaccine to immunize an animal against diseases associated with an infectious agent, and in particular, against tetanus, as a vaccine for the treatment and/or prevention of tetanus, is provided.

2. Related Art

Aluminum hydroxide and aluminum phosphate (collectively referred to as alum) are routinely used as adjuvants in human and veterinary vaccines (1). The efficacy of alum in increasing antibody responses to diphtheria and tetanus toxins is well established (2) and Hepatitis B virus antigen vaccine has been adjuvinated with alum (3). While the usefulness of alum is well established for some applications, it has limitations. For example, alum is a poor inducer of Th1 cellular immune responses and stimulates the production of antibodies, which is consistent with Th2 cellular immune response (4-6). Unfortunately, a Th2 based immune response is not likely to offer optimal protection against several important infectious diseases, including tuberculosis (TB), human immunodeficiency virus (HIV) and hepatitis C virus (HCV). Alum is poorly effective for influenza vaccination and inconsistently elicits a cell mediated immune response. The antibodies elicited by alum-adjuvinated antigens are mainly of the IgG1 isotope in the mouse, which may be optimal for protection by some vaccinal agents.

Tetanus is an important human and animal disease characterized by painful, uncontrolled muscle spasms, and death due to paralysis of the respiratory muscles. This disease is associated with infection by *Clostridium tetani* and prophylactic vaccination is common. Vaccines of many types, including tetanus vaccines, typically use alum as an adjuvant.

A need continues to exist in the medical arts for alternative vaccine adjuvant materials that may be used to enhance and/or improve existing clinical vaccine preparations for treatment and prophylaxis of disease associated with infectious agents and toxins. Adjuvant alternatives having superior characteristics to alum and other standard adjuvant materials are presented as part of the present invention, and present improved vaccines for many infectious agents and toxins, including tetanus.

SUMMARY OF THE INVENTION

The present invention was developed in part by the inventors' recognition of the robust inflammatory response invoked by an extracellular matrix material (ECM) preparation, described herein as a heterologous acellular collagenous tissue preparation prepared from mammalian tissue. While not intending to be limited to any particular mechanism of action, the adjuvants of the present invention demonstrate a robust inflammatory response, in part attributable to the antigenic diversity of the adjuvant preparations. The diverse nature of the components that make up the adjuvant preparations include different collagen species, proteins and other components. This feature is contemplated to contribute at least in part to the exponentially enhanced immune response demonstrated in animals exposed to the present preparations with the antigen toxin or infectious agent of interest, especially compared to vaccine preparations with alum as adjuvant.

The adjuvant described herein as a heterologus acellular collagenous tissue preparation comprise several different collagens (Types I, III, IV, V, VI), glycosaminoglycans (e.g., hyaluronic acid, chondroitin sulfate A and B, and heparin), proteoglycans (e.g., hyaluronan, heparan sulfate), glycoproteins (e.g., fibronectin and laminin), and growth factors (e.g., FGF-2, TGF-β, and CTGF), as well as matricellular proteins, such as thrombospondins, osteopontin, tenascins and elastin, among other proteins. The adjuvant preparations are processed through a disinfection protocol and a decellularization process that render them suitable for use in pharmaceutically acceptable vaccine and other preparations.

The contribution of pro-inflammatory species provided by the diverse nature of the adjuvant is contemplated to enhance the drive of the immune response to the antigenic species of interest (infectious pathogen or biological toxin). The present adjuvant preparations described as part of the invention harnesses the inflammatory-provoking activity of these diverse components to provide an immunopotent infectious agent vaccine preparation and infectious agent adjuvant.

The heterologous acellular collagenous tissue preparation, and materials like it, may be used in combination with any infectious pathogen or biological toxin of interest to provide a vaccine or other treatment preparation of interest. By way of example, and in some embodiments, the biological toxin of interest may comprise tetanus toxin. By further way of example, and in some embodiments, the biological toxin may comprise ricin.

The present invention is unique in that, among other things, it provides as part of a pharmaceutical compositions an adjuvant that contains many different and biologically distinct species of materials. By way of example, an adjuvant that is heterologously diverse is created by the processing of a tissue having a three-dimensional extracellular matrix material, this tissue being modified/processed to provide an adjuvant that includes a non-denatured family of different collagen types, proteins, and growth factors. By way of example, and in some embodiments, the adjuvant may be then used to provide a vaccine such as a tetanus vaccine. The invention thus provides in some embodiments improved vaccine preparations useful to vaccinate an animal against an infectious agent of interest. The adjuvant is demonstrated to enhance the biological activity of the vaccine antigen, while also maintaining an improved biocompatibility in vivo.

The extracellular matrix material in some embodiments is described as a heterologous acellular collagenous tissue preparation prepared from a mammalian tissue. By way of example and not limitation, such a mammalian tissue may comprise a small intestinal submucosa (SIS) tissue. However, it is anticipated by the present inventors that the heterologous acellular collagenous tissue preparations may be prepared and/or manufactured from many different types of tissues and/or biocompatible materials to provide an adjuvant having the enhanced immunogen provoking activity demonstrated with the presently disclosed adjuvants.

The vaccine preparations of the present invention comprising the unique adjuvants are demonstrated to enhance resistance to diseases associated with an infectious pathogen or biological toxin. In some embodiments, the present invention provides an adjuvant comprising a heterologous acellular collagenous tissue preparation that is in the form of a gel, sheet, liquid or particulate preparation. The adjuvant administered together with a toxin, for example an infectious tetanus toxoid confer protective immunity in vivo to animals challenged with tetanus toxin.

Infectious Agent Adjuvant

In one aspect, the present invention provides an adjuvant preparation that comprises an extracellular matrix (ECM) material. The extracellular matrix material may be further described as comprising a heterologous acellular collagenous tissue preparation. By way of example, and not limitation, such an acellular collagenous tissue preparation may be prepared from clinically processing an appropriate mammalian tissue. By way of example, such an appropriate mammalian tissue may include small intestinal submucosa (SIS), renal capsule material (RCM), according to the methods described herein. In some embodiments, the present preparations may be described as essentially free of alum. In some embodiments, the heterologous acellular collagenous tissue preparations may be described as a modified preparation of extracellular matrix material. In some embodiments, the adjuvant will be diluted in an appropriate pharmaceutically acceptable diluent to provide the desired adjuvant to antigen ratio. In some embodiments, the adjuvant preparation may be diluted about 2-fold to about 20-fold in a pharmaceutically acceptable diluent, such as sterile saline.

Infectious Agent Vaccine

In another aspect, the present invention provides an infectious agent vaccine comprising a preparation of the adjuvant comprising a heterologous acellular collagenous tissue preparation, together with a preparation of an antigen of an infectious pathogen.

In some embodiments, the adjuvant composition may be described as comprising an immunogenically enhancing preparation characteristic of an extracellular matrix material (ECM), particularly a preparation comprising an extracellular matrix derived from small intestinal submucosa (SIS) or renal capsule material (RCM). In particular embodiments, the adjuvant composition comprises an extracellular matrix material comprising a small intestinal submucosa tissue preparation.

In some preparations, the adjuvant composition comprises 1 part of an extracellular matrix material (ECM) and 9 parts of a pharmaceutically acceptable carrier solution. By way of example, such a pharmaceutically acceptable carrier solution is sterile saline.

According to another embodiment of the invention, there is provided a vaccine preparation comprising an adjuvant and a toxoid antigen of interest. In some embodiments, the vaccine may be described as a vaccine to protect against infectious pathogens, such as a tetanus vaccine, an influenza vaccine, a rabies vaccine, a viral hepatitis vaccine, a diphtheria vaccine, an anthrax vaccine, a *Streptococcus pneumonia* infection vaccine, a malaria vaccine, a leishmaniasis vaccine, or a Staphylococcal enterotoxin B toxicosis vaccine.

Biological Toxins

Examples of the biological toxins that may be used in the preparation of the vaccines of the present invention are: Abrin, Aflatoxins, Botulinum toxins, *Clostridium perfringens* episilon toxin, Conotoxins, Diacetoxyscirpenol, Ricin, Saxitoxin, Shigatoxin, Staphylococcal enterotoxins, Tetrodotoxin, T-2 Toxin, Diptheria toxin, Streptococcal toxins, Cholera toxin, Pertussis toxin, and Pneumolysin.

In particular embodiments, the vaccine may be described as a vaccine to protect against diseases associated with biological toxins, such as ricin.

Prion-Associated Diseases

In some embodiments, the invention provides an adjuvant preparation that is suitable for use in combination with a prion-associated disease. By way of example, such prion associated diseases include, all of which are classified as transmissible spongiform encephalopathies, bovine spongiform encephalopathy, scrapie, cervid chronic wasting disease and Creutzfeld-Jakob disease.

In other embodiments, the invention may be described as providing a vaccine to protect against disease associated with a viral infection. By way of example, the vaccines of the present invention may be formulated to provide a composition useful in the treatment and/or prevention of viral infections associated with influenza, rabies and viral hepatitis.

In other embodiments, the invention may be described as providing a vaccine to protect against diseases associated with a bacterial infection. By way of example, the vaccines of the present invention may be formulated to provide a composition useful in the treatment and/or prevention of bacterial infections associated with diseases such as diphtheria, anthrax, sepsis, pneumonia, otitis media and meningitis.

In yet other embodiments, the invention may be described as providing a vaccine to protect against diseases associated with a parasitic infection. By way of example, the vaccines of the present invention may be formulated to provide a composition useful in the treatment and/or prevention of a parasitic infection associated with the diseases of malaria and leishmaniasis.

In other embodiments, the invention may be described as providing a vaccine to protect against illnesses and/or diseases associated with exposure to a biological toxin. By way of example, the vaccines of the present invention may be formulated to provide a composition useful in the treatment and/or prevention of illness associated with exposure to biological toxins such as ricin (that causes respiratory distress) or exposure to Staphylococcal enterotoxin B (SEB) (that results in food poisoning).

Method of Preparing a Adjuvant and a Vaccine

In another aspect, the invention provides a method for preparing an infectious agent vaccine. In some embodiments, the method comprises preparing an adjuvant comprising a heterologous acellular collagenous tissue as described herein, and combining the adjuvant with an immunizing antigen of interest. In some embodiments, the antigen of interest is a tetanus toxoid preparation.

Methods of Preventing, Treating, Inhibiting, and/or Immunizing an Animal Against an Infectious Pathogen According to yet another broad aspect of the invention, a method for treating an animal having an infectious disease or at risk of contracting a disease or illness associated with exposure to an infectious pathogen. By way of example, diseases associated with exposure to an infectious pathogen include tetanus, malaria, diphtheria, anthrax, sepsis, pneumonia, otitis media and meningitis. In some embodiments, the invention provides a method for immunizing an animal against tetanus. In yet another embodiment, the invention provides a method for inhibiting the severity of tetanus and/or preventing the onset of tetanus altogether in an animal, the method comprising administering to an animal an immune provoking dose or doses of a vaccine comprising an adjuvant comprising a heterologous acellular collagenous tissue preparation and a suitable amount of the tetanus inducing infectious pathogen.

Clinical Infectious Pathogen Treatment Preparations

In yet another aspect, the invention provides a variety of unique infectious pathogen treatment preparations. These infectious agent treatment preparations may take the form of a gel, a sheet, a liquid or an injectable preparation suitable for parenteral administration, combined with an appropriate antigen of interest.

The following abbreviations are used throughout the description of the present invention: ECM—Extracellular Matrix; HCV—Hepatitis C Virus; HV—Human Immunodeficiency Virus; RCM—Renal Capsule Material; SIS—Small Intestinal Submucosa; and TB—Tuberculosis.

BRIEF DESCRIPTION OF THE DRAWINGS

FIG. 5 is a graph showing serum tetanus toxoid titers as measured by mean O.D. at 450 nm based on reciprocal dilutions of serum as represented by:

| | Reciprocal Dilution of Serum | | | | |
|---|---|---|---|---|---|
| | Log-Logit Fit: $y = (A - D)/(1 + (X/C)^B + D$: | A | B | C | D | R^2 |
| ○ | Saline (Group 01: Dilution vs Mean O.D.) | 0.012 | 0 | 0 | −0.00341 | 0 |
| □ | antiI-TT (Group 02: Dilution vs Mean O.D.) | −0.00251 | 0 | 0 | −0.00391 | 0 |
| △ | TT + ALUM (Group 03: Dilution vs Mean O.D.) | 1.05 | 0.829 | 1.92e+03 | 0.144 | 0.928 |
| ◇ | TT + Particulate (Group 04: Dilution vs Mean O.D.) | 1.11 | 0.985 | 4.54e+03 | 0.282 | 0.891 |
| ● | TT + Gel (Group 05: Dilution vs Mean O.D.) | 1.16 | 1.02 | 3.42e+03 | 0.221 | 0.946 |
| ■ | Particulate Alone (Group 06: Dilution vs Mean O.D.) | 0.0457 | 1.19 | 232 | −0.0013 | 0.975 |
| ▲ | Gel Alone (Group 07: Dilution vs Mean O.D.) | 0.0684 | 1.01 | 226 | 0.00295 | 0.884 |
| ◆ | Control Serum (Group 08: Dilution vs Mean O.D.) | 1.07 | 0.884 | 3.68e+03 | 0.223 | 0.935 |

Figure 1:
FIG. 1, according to some embodiments of the invention, presents a remnant of SIS extracellular matrix material in a rat 28 days after surgical implantation. The remaining biomaterial is surrounded by macrophages with occasional lymphocytes. Stained with H & E, 400X.
Figure 2:
FIG. 2, according to some embodiments of the invention, presents the focus of mononuclear inflammation at the interface of an implant/tendon surface in a rat which underwent repair of Achilles tendon defect with RCM 7 days earlier. Stained with H & E, 200X.
Figure 3:
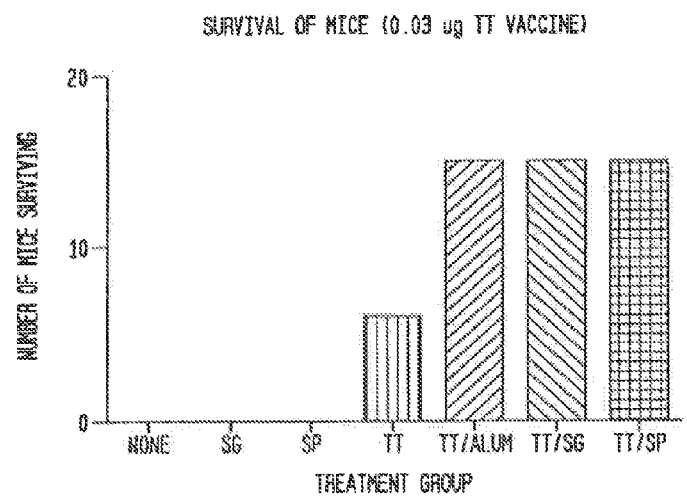
FIG. 3, according to some embodiments of the invention, presents the survival data of mice, vaccinated with 0.03 micrograms of tetanus toxoid, following challenge with 1 ng/mouse of tetanus toxin intraperitoneally. Treatment groups are untreated (None); SIS gel (SG); SIS particulate (SP); tetanus toxoid (TT); TT with alum (TT/Alum); TT with SIS gel (TT/SG); and TT with SIS particulate (TT/SP). Each group consisted of 15 mice. All mice which were untreated or vaccinated with only SIS gel or SIS particulate died; six mice vaccinated with unadjuvanted tetanus toxoid survived, and all mice vaccinated with tetanus toxoid in alum, SIS gel, or SIS particulate survived. This represents a significant ($P<0.001$) increase in number of mice surviving for the latter three groups compared to all other groups.
Figure 4:
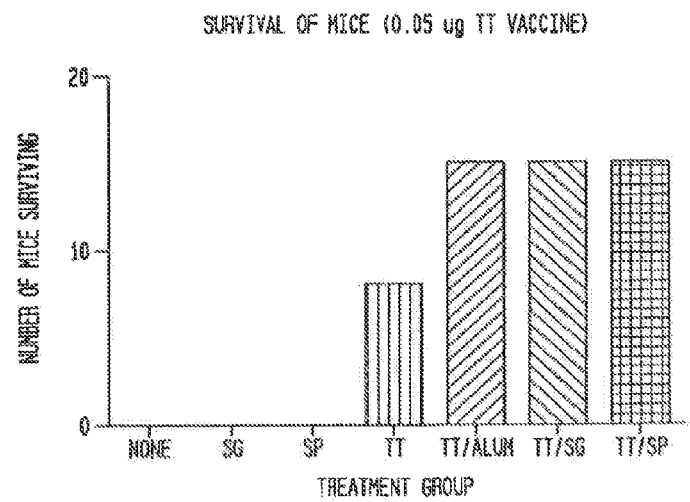
FIG. 4, according to some embodiments of the invention, presents survival data of mice, vaccinated with 0.05 micrograms of tetanus toxoid, following challenge with 1 ng/mouse of tetanus toxin intraperitoneally. Treatment groups are untreated (None); SIS gel (SG); SIS particulate (SP); tetanus toxoid (TT); TT with alum (TT/Alum); TT with SIS gel (TT/SG); and TT with SIS particulate (TT/SP). Each group consisted of 15 mice. All mice which were untreated or vaccinated with only SIS gel or SIS particulate died; eight mice vaccinated with unadjuvanted tetanus toxoid survived; and all mice vaccinated with tetanus toxoid in alum, SIS gel, or SIS particulate survived. This represents a significant ($P<0.001$) increase in number of mice surviving for the latter three groups compared to all other groups.
Figure 5:
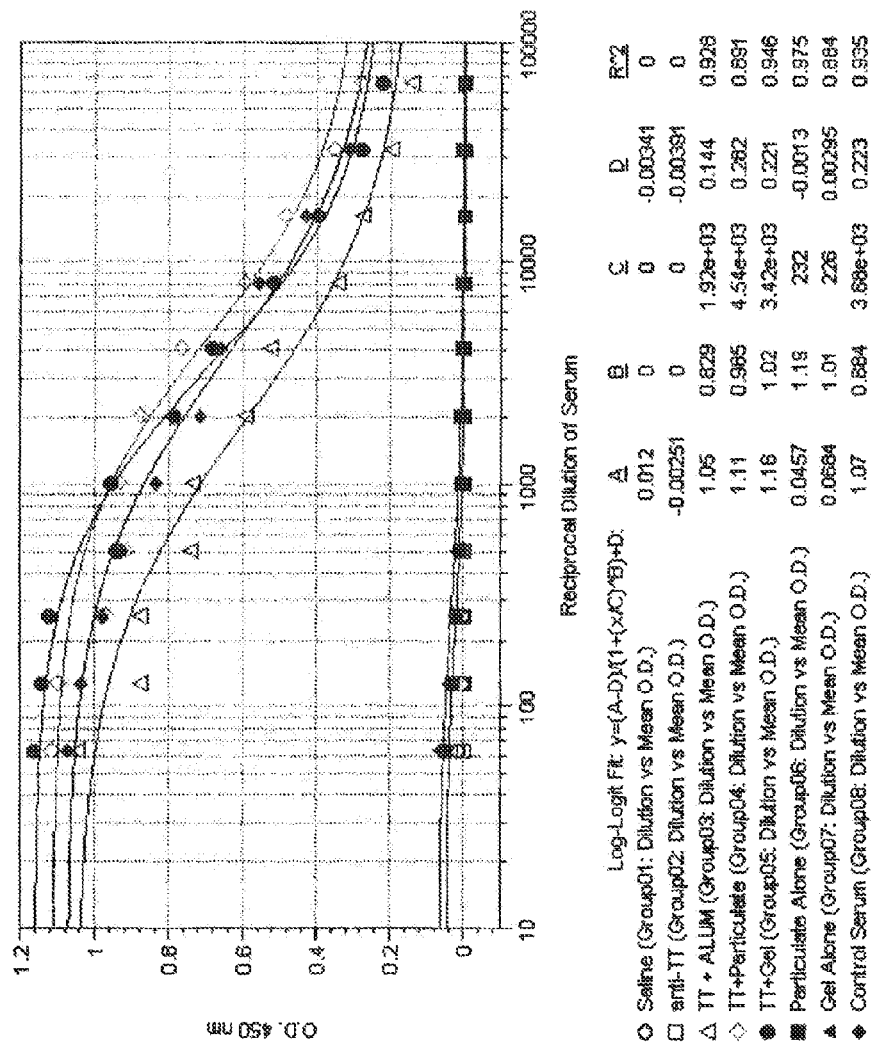
Figure 6:
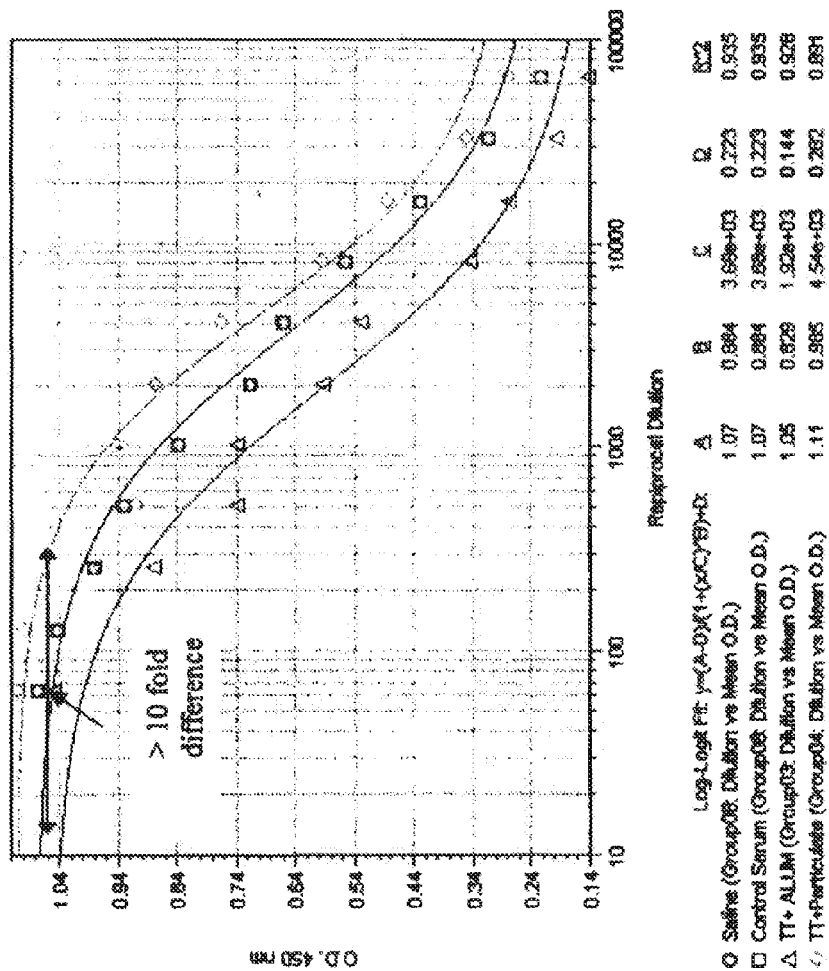

FIG. 6 is a graph showing serum tetanus toxoid titers in groups treated with alum versus SIS particulate as measured by means O.D. at 450 nm based on reciprocal dilutions of serum as represented by:

| Reciprocal Dilution | | | | | |
|---|---|---|---|---|---|
| Log-Logit Fit: y = (A − D)/(1 + (X/C)^B) + D: | A | B | C | D | R^2 |
| ○ Saline (Group 06: Dilution vs Mean O.D.) | 1.07 | 0.884 | 3.88e+03 | 0.223 | 0.935 |
| □ Control Serum (Group 08: Dilution vs Mean O.D.) | 1.07 | 0.884 | 3.88e+03 | 0.223 | 0.935 |
| △ TT + ALUM (Group 03: Dilution vs Mean O.D.) | 1.05 | 0.829 | 1.92e+03 | 0.144 | 0.928 |
| ◇ TT + Particulate (Group 04: Dilution vs Mean O.D.) | 1.11 | 0.985 | 4.54e+03 | 0.282 | 0.891 |

Figure 7:
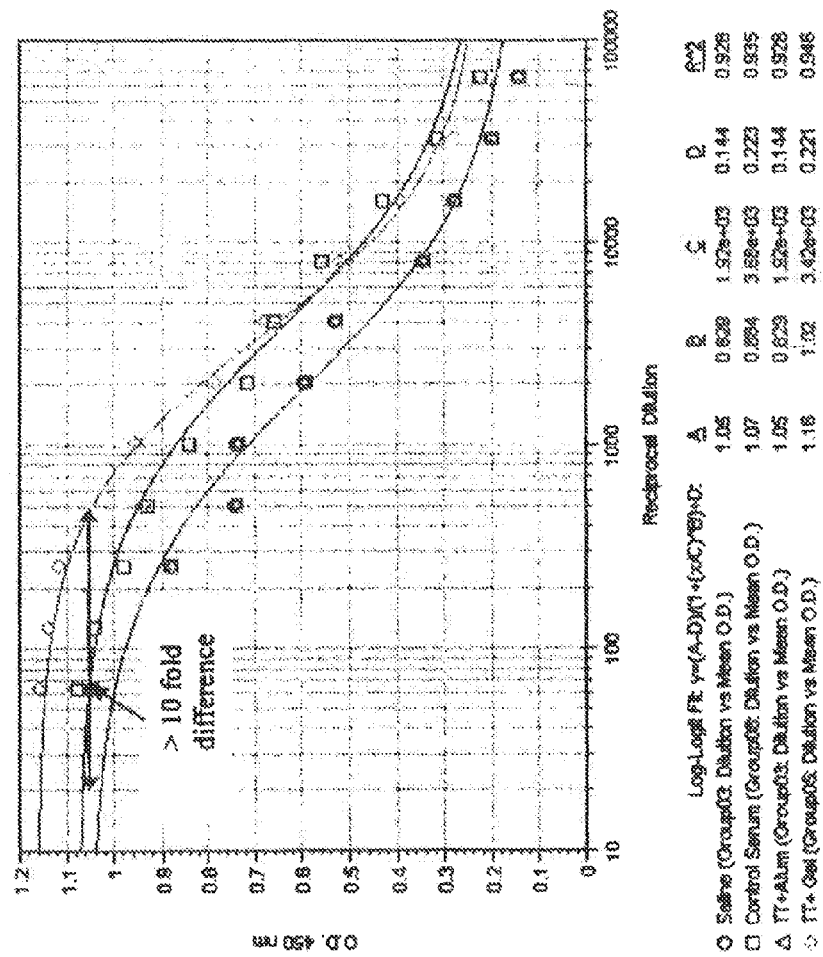

FIG. 7 is a graph showing serum tetanus toxoid titers in groups treated with alum versus SIS gel as measured by means O.D. at 450 nm based on reciprocal dilutions of serum as represented by:

| Reciprocal Dilution | | | | | |
|---|---|---|---|---|---|
| Log-Logit Fit: y = (A − D)/(1 + (X/C)^B) + D: | A | B | C | D | R^2 |
| ○ Saline (Group 03: Dilution vs Mean O.D.) | 1.05 | 0.829 | 1.92e+03 | 0.144 | 0.928 |
| □ Control Serum (Group 08: Dilution vs Mean O.D.) | 1.07 | 0.884 | 3.68e+03 | 0.223 | 0.935 |
| △ TT + ALUM (Group 03: Dilution vs Mean O.D.) | 1.05 | 0.829 | 1.92e+03 | 0.144 | 0.928 |
| ◇ TT + Gel (Group 05: Dilution vs Mean O.D.) | 1.16 | 1.02 | 3.42e+03 | 0.221 | 0.946 |

DETAILED DESCRIPTION OF THE INVENTION

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

For the purposes of the present invention, the term "adjuvant" is defined as a substance which enhances the immune response to an antigen.

For purposes of the present invention, the term, "adjuvancy" is defined as the ability of an agent to enhance and/or promote the immune response of animal to a particular antigen.

For the purposes of the present invention, the term "biosynthetic material" is defined as a material that is in part or whole made up from or derived from a biological tissue.

For purposes of the present invention, the term "biological tissue" is defined as an animal tissue, including human, or plant tissue that is or that once was (cadaver tissue, for example) part of a living tissue or organism.

For the purposes of the present invention, the term "extracellular matrix" or "ECM" is defined as a tissue derived or bio-synthetic material that is capable of supporting the growth of a cell or culture of cells.

For the purposes of the present invention, the term "heterologous acellular collagenous material" is defined as an acellular (without cells), collagenous material that comprises at least collagen types I, III, IV, V and V, growth factors, fibronectin, glycoproteins, glycosaminoglycans and laminin, and that is suitable for use as an adjuvant.

For the purposes of the present invention, the term "infectious agent" is defined as any bacterial, viral, prion or parasitic agent capable of causing disease in humans or animals subsequent to infection or secretion of a substance, such as the production of a toxin or toxins. This term also includes the toxic products of such agents. By way of example, such an infectious agent includes *clostridium botulinum*, the causative agent of tetanus.

For the purposes of the present invention, the term "heterologous acellular collagenous material" is defined as an acellular (without cells), collagenous material that comprises at least collagen types I, III, IV, V and VI, growth factors, fibronectin, glycoproteins, glycosaminoglycans and laminin, and that is suitable for use as an adjuvant.

For the purposes of the present invention, the term, "immunogenic amount" is an amount of an infectious pathogen antigen preparation of interest or amount of a biological toxin that elicits a clinically detectable protective response in an animal. By way of example, a clinically detectable protective response in an animal may be the production of an elevated titer of antibodies in the animal specific for the infectious pathogen antigen or biological toxin.

The description of the present invention is enhanced by the various examples that follow.

EXAMPLE 1

Materials and Methods for ECM as an Adjuvant for a Vaccine Against Diseases Associated with an Infectious Pathogen The present example provides some examples of materials and methods that may be used in the practice of the present invention.

Small Intestinal Submucosa (SIS)

Small Intestinal Submucosa (SIS) was obtained from Cook Biotech, Inc. (West Lafayette, Ind.). Experimental grade material was provided for use in the present studies of an SIS preparation that was described as having been prepared by harvesting porcine jejunum and placing 10- to 20-cm lengths into saline solution (31-33). Following removal of all mesenteric tissues, the jejunal segment was everted and the tunica mucosa abraded using a longitudinal wiping motion with a scalpel handle and moistened gauze. The serosa and tunica muscularis were then gently removed using the same procedure. The remaining tissue was disinfected with peracetic acid, rinsed extensively in high purity water, and sterilized using ethylene oxide. SIS Particulate is supplied by Cook Biotech, Inc. (West Lafayette, Ind.) and is SIS material ground and sieved. The size particles are in the range from 45 micron to 335 micron. SIS gel is supplied by Cook Biotech, Inc. (West Lafayette, Ind.) and is produced from SIS material via an acid digestion and purification process.

Tetanus Toxin and Tetanus Toxoid

Tetanus toxin and tetanus toxoid were purchased from List Biological Laboratories (Campbell, Calif.).

Alum

Alum was purchased as Alhydrogel®, an aluminum hydroxide gel adjuvant (Brenntak Biosector, Frederikssund, Denmark).

Animals (Mice)—Statistical Analysis

Results of survival versus non-survival following challenge with tetanus toxin were compared between groups using the Chi-square test with two degrees of freedom. Differences were considered significant when $p<0.001$.

EXAMPLE 2

Use of Adjuvant in the Inhibition of Tetanus

To determine if SIS can act as an adjuvant for vaccines against diseases associated with infectious pathogens or biological toxins, preparations were made with tetanus toxoid, an inactivated form of tetanus toxin. Both gel SIS and SIS particles produced from a sheet of single layer SIS were evaluated as adjuvants. Briefly, groups of 15 Balb/C female mice (Harlan, Inc., Indianapolis, Ind.) were vaccinated initially (0.1 ml volume/dose) and again, five weeks later with one of the following: Particulate SIS; Gel SIS; Tetanus toxoid (TT; 0.03 ug/dose), TT (0.05 ug/dose), TT (0.03 ug/dose)+ alum (alhydrogel), TT (0.05 ug/dose)+alum (alhydrogel), TT (0.03 ug/dose)+particulate SIS; TT (0.05 ug/dose)+particulate SIS, TT (0.03 ug/dose)+gel SIS, TT (0.05 ug/dose)+gel SIS, and Untreated control group.

Five weeks after the second vaccination, mice were challenged with a lethal dose of tetanus toxin (1 ng/mouse) given intraperitoneally in 0.2 ml of sterile saline. Mice were then observed over the next 96 hours and the number of surviving mice recorded for each group.

The results of this study are shown in Table 1 below.

TABLE 1

| Treatment Group | Number Surviving/ Total at 96 h |
|---|---|
| Untreated | 0/15 |
| Gel SIS | 0/15 |
| Particulate SIS | 0/15 |
| Tetanus toxoid (TT; 0.03 ug/dose) | 6/15 |
| TT (0.05 ug/dose) | 8/15 |
| TT (0.03 ug/dose) + alum (alhydrogel) | 15/15 |
| TT (0.05 ug/dose) + alum (alhydrogel) | 15/15 |
| TT (0.03 ug/dose) + particulate SIS | 15/15 |
| TT (0.05 ug/dose) + particulate SIS | 15/15 |
| TT (0.03 ug/dose) + gel SIS | 15/15 |
| TT (0.05 ug/dose) + gel SIS | 15/15 |

A significantly greater number of mice survived challenge with tetanus toxin in groups vaccinated with either 0.03 or 0.05 ug/dose of tetanus toxoid administered in alhydrogel, SIS gel, or particulate SIS compared to all other vaccination groups.

These results demonstrate the ability of both particulate and gel SIS to act as an adjuvant for a vaccine against disease associated with an infectious pathogen, such as tetanus.

EXAMPLE 3

Elevation of Tetanus Toxoid Serum Titers in the Presence of ECM Adjuvant

Groups of 15 Balb/c 8-10 week old female mice (Harlan, Indianapolis, Ind.) were used for these studies and divided into the groups as shown in Table 2 below.

TABLE 2

| Inoculated Groups of Mice | |
|---|---|
| Group # | Treatment |
| 1 | Saline |
| 2 | Tetanus Toxoid (TT; 3 μg/dose) |
| 3 | TT (0.05 μg/dose) + alum |
| 4 | TT (0.05 μg/dose) + particulate SIS |
| 5 | TT (0.05 μg/dose) + gel SIS |
| 6 | 300 μg particulate SIS |
| 7 | 300 μg particulate SIS |
| 8 | Control serum |

Mice were vaccinated initially and again five weeks later. At weeks 6 and 10, serum was collected from each group and pooled. Each group contained 15 animals. The pooled serum was analyzed for anti-tetanus toxoid (TT) immunoglobulin by standard ELISA screening. The results of the testing of the TT plus alum and TT plus particulate SIS groups were repeated. The serum antibody titer levels of TT immunoglobulin in each of the treatment groups is illustrated in FIG. 5.

The results shown in FIG. 5 demonstrate that treatment of animals with ECM tissue as adjuvant and antigen (TT) vaccine provoked a significant immune response evidenced by a potent stimulation of serum antibody titer levels in vivo. The serum antibody titer levels observed in the ECM-antigen treated animals (SIS/TT) were significantly higher than serum antibody titer levels in the alum-antigen treated animals.

As shown in FIG. 6, ECM tissue as adjuvant (SIS particulate) combined with tetanus toxoid antigen (TT) provoked a significant immune response, resulting in an increase in serum antibody titer levels 10-fold greater than the serum antibody titer levels observed in animals treated with alum as adjuvant and antigen (TT).

As shown in FIG. 6, ECM tissue as adjuvant (SIS gel) combined with tetanus toxoid antigen (TT) provoked a significant immune response resulting in an increase in serum antibody titer levels 10-fold greater than serum antibody titer levels observed in animals treated with the conventional alum adjuvant combined with TT antigen.

The differences in serum antibody titer levels between extracellular matrix as adjuvant and alum as adjuvant represent a significant therapeutic advantage over the use of alum, as the extracellular matrix materials are demonstrated to be more efficacious adjuvant than alum. In addition, the extracellular matrix materials are also more cost effective than alum for the preparation of vaccines. Thus, smaller (less) amounts of the antigen of interest, such as for example, tetanus toxoid (TT) antigen, may be used as part of a vaccine without loss of therapeutic potential in the generation of similar serum titer levels of antibody in vivo. This is of particular advantage in the formulation of vaccines that would include, for example, a recombinant protein as antigen, that are more expensive and/or in shorter supply.

The results from this experiment show that extracellular matrix is a potent adjuvant and can enhance immunogenicity of an infectious pathogen or biological toxin. Accordingly, ECM is suitable for use as an adjuvant in a vaccine preparation, and effectively provokes immune response as demonstrated by elevated serum levels in the animals tested.

EXAMPLE 4

Exemplary Infectious Pathogens

The present example demonstrates the utility of the present invention with disease associated with a wide variety of infectious pathogens and biological toxins, including by way of example and not exclusion, tetanus, influenza, rabies, viral hepatitis, diphtheria, anthrax, *Streptococcus pneumoniae* infection, malaria, leishmaniasis, ricin toxicosis, and Staphylococcal enterotoxin B toxicosis.

TABLE 3

Classification of Common Vaccines for Humans

| Disease or Pathogen | | Type of Vaccine |
|---|---|---|
| Whole Organisms: | | |
| Bacterials Cells: | Cholera | Inactivated |
| | Plague | Inactivated |
| | Tuberculosis | Attenuated BCG[+] |
| | *Salmonella typhi* | Attenuated |
| Viral Particles: | Influenza | Inactivated |
| | Measles | Attenuated |
| | Mumps | Attenuated |
| | Rubella | Attenuated |
| | Polio (Sabin/OPV) | Attenuated |
| | Polio (Salk/IPV) | Inactivated |
| | *V. zoster* | Attenuated |
| | Yellow fever | Attenuated |
| Type of Vaccine (Purified Macromolecules) | | |
| Toxoids: | Diptheria | Inactivated exotoxin |
| | Tetanus | Inactivated exotoxin |
| | Acellular Pertussis | Inactivated exotoxin |
| Capsular Polysaccharide: | *Haemophilus influenza b* | Polysaccharide + protein carrier |
| | *Neisseria meningidis* | Polysaccharide + protein carrier |
| | *Streptococcus pneumoniae* | 23 distinct capsular polysaccharides |
| Surface Antigen: | Hepatitis B | Recombinant surface antigen (HbsAg) |

[+]Bacillus Calmette-Guerin (BCG) is an antiviral strain of *Mycobacterium bovis*.

Vaccines for Disease Associated with Viral Infections

1. Influenza—Influenza is an acute febrile respiratory disease resulting from infection with the influenza virus. Current influenza vaccines use aluminum adjuvants. To enhance the efficacy of vaccines, several adjuvants have been examined. For example, the oil-in-water emulsion MF59 has been reported to improve vaccine immunity (Higgins (1996)[1]; Martin (1997)[2], though it does not completely solve the low efficiency of the influenza vaccine in the elderly (Banzhoff (2003)[3]). A synthetic peptide, GK1, derived from *Taenia crassiceps cysticerci* was reported to enhance the immune response accompanying influenza vaccination in both young and aged mice (Segura-Velasquez (2006).sup.4), but trials in humans have not been published.

As part of the present invention, an influenza vaccine may be provided that comprises the extracellular matrix material described herein as the vaccine adjuvant combined with an immunologically effective amount of an influenza antigen. By way of example, such an influenza antigen may comprise a current influenza virus combination of antigens of an H5N1 (hemagglutinin [HA] subtype 1; neuraminidase [NA] subtype 1), and H3N2 influenza A virus, and an influenza B virus. This preparation and other influenza antigen preparations are described in Palese (2006)[33]). This article and all of its teachings are incorporated herein by reference.

2. Rabies—Rabies is a devastating neurological disease that is caused by infection with the rabies virus. Vaccination against rabies typically utilizes inactivated virus and an aluminum adjuvant. A lipoid adjuvant of the oil-in-water type, based on squalene, significantly increased the immunologic response of mice to vaccination with an inactivated virus vaccine when compared to vaccination using an aluminum salt adjuvant (Suli, 2004). An adjuvant based on glycopeptidolipids extracted from *Mycobacterium cheloniae* enhanced the immune response of mice to vaccination with an inactivated rabies virus vaccine (de Souza Matos (2000)[6]).

As part of the present invention, a rabies vaccine may be provided that comprises the extracellular matrix material as the vaccine adjuvant combined with an immunologically effective amount of a rabies antigen. By way of example, a rabies antigen may comprise an inactivated rabies virus. One example of an inactivated rabies virus vaccine antigen that may be used in the present formulations is described in de Souza Matos (2000)[6].

3. Viral Hepatitis—Viral hepatitis, particularly that caused by Hepatitis B virus, is a serious health problem with over 300 million people affected worldwide. Vaccination offers hope for effective prophylaxis. Peptide epitopes of the virus stimulated a significant immune response when fused with heat shock protein 70 from *Mycobacterium tuberculosis* as an adjuvant (Peng (2006)[7]). Unmethylated CpG dinucleotides were effective as an adjuvant with hepatitis B antigen in aged mice (Qin (2004)[8]); and a vaccine consisting of hepatitis B virus antigens and an immunostimulatory DNA sequence is in human clinical trials (Sung (2006)[9]). In development of an intranasal vaccine, it was shown that DL-lactide/glycolide copolymer microspheres with chitosan were an effective adjuvant for a vaccine based on recombinant Hepatitis B surface protein (Jaganathan (2006)[10]).

As part of the present invention, a viral hepatitis vaccine may be provided that comprises the extracellular matrix material as the vaccine adjuvant combined with an immunologically effective amount of a viral hepatitis antigen. By way of example, such a hepatitis antigen may comprise recombinant hepatitis B surface protein. By way of example, such a hepatitis B surface protein antigen is described in Jaganathan, (2006)[10]), which reference is specifically incorporated herein by reference.

Vaccines for Disease Associated with Bacterial Infections

1. Diphtheria—A respiratory disease characterized by dysnepea, weakness, and pyrexia, diphtheria is the result of infection with *Corynebacterium diphtheriae*, bacteria which produces a toxin that is carried hematogenously through the body. Immunization against diphtheria is frequently combined with immunization against tetanus and pertussis; these vaccines typically contain aluminum salt adjuvants (Sugai (2005)[11]). Unmethylated CpG dinucleotides were effective as an adjuvant in a diphtheria-tetanus-pertussis vaccine and shifted the immune response toward cell-mediated immunity in mice immunized intraperitoneally (Sugai (2005)[11]). Trials to reduce adverse side-effects related to the aluminum salt adjuvant of a vaccine consisting of diphtheria toxoid, tetanus toxoid, and purified *Bordetella pertussis* antigens including pertussis toxoid showed that reduction of the aluminum salt content of the vaccine resulted in reduced geometric mean antibody concentrations to the relevant antigens, but did not result in reduction of local or general side effects (Theeten (2005)[12]). Monophosphoryl lipid A was shown in mice to effectively serve as an adjuvant for diphtheria toxin in mice (Caglar (2005)[13]).

As part of the present invention, a diphtheria vaccine may be provided that comprises the extracellular matrix material as the vaccine adjuvant combined with an immunologically effective amount of a diphtheria antigen. By way of example, a diphtheria antigen may comprise a diphtheria toxoid. One example of a diphtheria toxoid that may be used in the practice of the present invention is described in Theeten (Theeten (2005)[12].

2. Anthrax—Anthrax is a disease caused by the bacterium, *Bacillus anthracis*. Specifically, the bacterium produces a toxin which results in hemorrhagic necrosis of lymph nodes, hematogenous spread, shock, and death. A vaccine consisting of one subunit (protective antigen) of this toxin was shown to protect mice when combined with a microparticle adjuvant administered by either the intramuscular or intranasal routes (Flick-Smith (2002)[14]). Further, vaccination protected mice against infection with *B. anthracis* spores. While the aluminum salt-adjuvanted anthrax-vaccine-adsorbed is the only anthrax vaccine licensed in the United States, major drawbacks exist, including a very lengthy and complicated dosing schedule, followed by annual booster injections. Further, the aluminum adjuvant of anthrax vaccine has been linked to Gulf War Illness among veterans of the 1991 conflict (Petrik (2007)[15]).

As part of the present invention, an anthrax vaccine may be provided that comprises the extracellular matrix material as the vaccine adjuvant combined with an immunologically effective amount of an anthrax antigen. By way of example, such an anthrax antigen may comprise the one subunit (protective antigen) of the *Bacillus anthracis* bacterium. One such particular antigenic subunit is described in Flick-Smith (2002)[14].

3. *Streptococcus pneumoniae*—A bacterial pathogen of particular importance to the elderly and young adults, *Streptococcus pneumoniae* causes disease including sepsis and pneumonia, otitis media and meningitis. Vaccines typically involve adsorption of *S. pneumoniae* antigens to aluminum salt adjuvants, and reduced aluminum salt content led to reduced immunogenicity of *S. pneumoniae* vaccines (Levesque (2006)[16]). In human trials, IL-12 failed to improve the immune response to a pneumococcal polysaccharide vaccine; and IL-12 was associated with a high incidence of local and systemic side effects in humans (Hedlund (2002)[17]). Intranasal immunization against *S. pneumoniae* has been shown to be an effective method for preventing infection and disease, with unmethylated CpG dinucleotides serving as an effective adjuvant for an intranasal polysaccharide-protein conjugate vaccine (Sen (2006)[18]). Likewise, IL-12 and the B-subunit of cholera toxin were both shown to enhance efficacy of intranasally-administered preparations of *S. pneumoniae* antigens (Sabirov (2006)[19]; Pimenta (2006)[20]).

As part of the present invention, a pneumonia vaccine may be provided that comprises the extracellular matrix material described herein as the vaccine adjuvant combined with an immunologically effective amount of a pneumococcal antigen. By way of example, such a pneumococcal antigen may comprise a pneumococcal polysaccharide antigen. One form of a pneumococcal polysaccharide antigen is described in Hedlund (2002)[17]. This pneumococcal antigen may used as part in combination with the herein described adjuvants in a vaccine preparation.

Vaccines for Diseases Associated with Parasitic Infections

1. Malaria—Malaria affects millions of people worldwide and each year, 1-2 million people die from the disease caused by *Plasmodium falciparum*. Thus, the need for prophylactic measures has led to great interest in anti-malaria vaccines. The apical membrane antigen, a malaria vaccine candidate, was reported to have an enhanced immunogenicity by the aluminum salt adjuvant Alhydrogel (HCl Biosector, Denmark); and this adjuvant effect was further enhanced, and shifted from a Th1 response to a mixed Th1/Th2 response, by inclusion of the adjuvant CpG oligodeoxynucleotide (Mullen (2006)[21]). Alhydrogel and Montanide ISA 720 (Seppic, France) were compared in rhesus monkeys as adjuvants for a vaccine based on protective epitopes from the circumsporozoite protein of *P. falciparum*. Though Montanide ISA 720 induced superior immune responses, the formation of sterile abscesses at injection sites were noted as a significant disadvantage (Langermans (2005)[22]). Other studies with a circumsporozoite protein vaccine conducted in rhesus monkeys showed that some novel oil-in-water adjuvants with components of immunostimulants 3-deacetylated monophosphoryl lipid A (3D-MPL) and the saponin *Quillaja saponaria* 21 (QS21) were safe and stimulated improved antibody responses (Stewart (2006)[23]). Some of these same oil-in-water adjuvants improved the immune response to a vaccine constructed of the *P. falciparum* antigen, Liver Stage Antigen-1 (Brando (2006)[24]).

As part of the present invention, a malarial vaccine may be provided that comprises the extracellular matrix material as the vaccine adjuvant combined with an immunologically effective amount of a malarial antigen. By way of example, such a malarial antigen may comprise a *P. falciparum* antigen Liver Stage Antigen-1. This antigen is described in detail in Brando (2006)[24], this article being specifically incorporated herein by reference. This antigen may be combined with the extracellular matrix material described herein as an adjuvant to provide an anti-malarial vaccine as described herein.

2. Leishmaniasis—Leishmaniasis is a parasitic disease associated with infection by a species of parasites from the *Leishmania* genus. A large spectrum of clinical disease forms can result from infection, ranging from cutaneous lesions to fatal visceral forms. In the absence of effective, non-toxic treatments, great effort has been given to vaccine development. Vaccines based on DNA of the parasite have been shown to induce partial protection; aluminum phosphate adjuvant has no effect on the humoral response to this vaccine, but has been reported to slightly increase the cellular immune response and protection against infection in a mouse model (Rosado-Vallado (2005)25). In evaluations in rhesus monkeys using a soluble *Leishmania* antigen and alum with IL-12 as adjuvants, it was shown that the adjuvants improved protective immunity, though transient nodules developed at the site of subcutaneous injection (Kenney (1999)[26]). CpG oligodeoxynucleotides served as an effective adjuvant for a vaccine consisting of live, nonattenuated *L. major* organisms alone or in combination with lysates of heat-killed *L. major* promastigotes, either without or bound to alum (Mendez (2003)[27]). Partial protective immunity was stimulated, but mice receiving alum-containing vaccines developed large dermal lesions that required up to 10 weeks to heal.

As part of the present invention, an anti-parasitic infection associated disease vaccine may be provided that comprises the extracellular matrix material as the vaccine adjuvant combined with an immunologically effective amount of a Leishmaniasis antigen, or any of the other antigenic species described above. By way of example, a Leishmaniasis antigen may comprise the Leishmaniasis antigen described in detail in Kenny (1999)[26], which article is specifically incorporated herein by reference.

Vaccines for Disease Associated with Biological Toxins

1. Ricin—Ricin is a toxin produced naturally by the seeds of the castor bean plant, *Ricinus communis*. When humans or animals are exposed to the toxin, severe respiratory distress and death may result. Because of its potency and ability to be administered via aerosol, ingestion, or injection, ricin is considered a powerful bioweapon. Though there is presently no approved commercial vaccine for ricin, pilot trials in humans have examined the use of recombinant, non-toxic forms of one of the subunits of ricin (Vitetta (2006)[28]). This preparation was administered without an adjuvant and elicited ricin-neutralizing antibodies in some of those tested, particularly at higher doses. However, all dose groups were found to result in significant side-effects, including myalgia and headache. Ricin toxoid adjuvantized by liposomal encapsulation was found to induce a stronger immune response when administered intra-tracheally than the vaccine adjuvantized with an aluminum salt adjuvant (Griffiths (1997)[29]). A vaccine consisting of a deglycosylated chain A ricin (DCAR) and the adjuvant LTR72, a mutant of the heat-labile enterotoxin of *Escherichia coli*, resulted in a stronger antibody response of vaccinated mice to ricin, but did not result in improved protection against lung injury when challenged with ricin (Kende (2006)[30]).

As part of the present invention, an anti-ricin vaccine may be provided that comprises the extracellular matrix material as the vaccine adjuvant as described herein combined with an immunologically effective amount of a ricin toxoid antigen. By way of example, such a ricin toxoid antigen is described in detail in Griffiths (1997)[29], which article is specifically incorporated herein by reference.

2. Staphylococcal enterotoxin B (SEB)—SEB is produced by the bacteria, *Staphylococcus aureus* and is associated with food poisoning. Incorporation of SEB toxoid into biodegradable poly(DL-lactide-co-glycolide) microspheres enhanced the immune response of mice to a degree similar to SEB toxoid adsorbed to alum and combined with complete Freund adjuvant (Eldridge, 1991)[31]). Similarly, SEB toxoid was effectively adjuvantized by incorporation into polylactic polyglycolic acid copolymer nanospheres; the resulting immune response was comparable to that achieved by using alum as an adjuvant (Desai (2000)[32]).

As part of the present invention, an anti-toxin-associated disease vaccine may be provided that comprises the extracellular matrix material as the vaccine adjuvant combined with an immunologically effective amount of an antigen such as ricin toxoid or SEB toxoid as antigen. By way of example, such antigens are described in detail in Vitetta (2006)[28] and Eldridge (1991)[31], the teachings of which are specifically incorporated herein by reference.

Vaccines for Diseases Associated with Prions

In some embodiments, the invention provides an adjuvant preparation that is suitable for use in combination with a prion-associated disease. By way of example, such prion associated diseases include, all of which are classified as transmissible spongiform encephalopathies, bovine spongiform encephalopathy, scrapie, cervid chronic wasting disease and Creutzfeld-Jakob disease.

Although prions use immune and lymphoreticular cells to gain access to the brain (Aguzzi, 2003)[36], existing evidence suggests that humoral immune responses can suppress infection. In particular, antibodies to the cellular prion protein (PrPc) are known to inhibit prion propagation (Petetz, 2001[37]; Enari, 2001[38]). Still, host tolerance to endogenous PrPc remains a major obstacle to active vaccination. In mice, vaccination with recombinant PrPc antigens such as peptides and polypeptides stimulated only weak immune responses. Co-administration of prion antigens with adjuvants such as Freund's (Polymenidou, 2004[39]; Koller, 2002[40]; Sigurddson, 2002[41]; Gilch, 2003[42]; Hanan, 2001[43]; Hanan, 2001[44]; Souan, 2001[45]; Arbel, 2003[46]); Montanide IMS-1313 (Schwartz, 2003[47]); TiterMax®, a combination of a proprietary block copolymer CRL-8941, squalene, a metabolizable oil, and a unique microparticulate stabilizer (Gilch, 2003[42]); and CpG oligonucleotides (Rosset, 2004[48]) all failed to induce strong immune responses.

It is anticipated that the presently described adjuvant preparations of an extracellular matrix material may be used with the prion protein (PrPc) to provide an improved vaccine against prion-associated infections.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The references listed below as well as all references cited in the specification are incorporated herein by reference to the extent that they supplement, explain, provide a background for or teach methodology, techniques and/or compositions employed herein.

1. Higgins D A, et al. (1996), Vaccine, 14:478-484.
2. Martin J T. (1997), Biologicals, 25:209-213.
3. Banzhoff A, Nacci P, Podda A. (2003), Gerontology, 49:177-184.
4. Segura-Velasquez R, et al. (2006), Vaccine, 24:1073-1080.
5. Suli J, et al. (2004), Vaccine 22:3464-3469.
6. de Souza Matos D C, et al. (2000), Vaccine, 18:2125-2131.
7. Peng M, et al. (2006), Vaccine, 24:887-896.
8. Qin W, et al. (2004), Cell Mol Immunol, 1:148-152.
9. Sung J J, et al. (2006), Curr Opin Mol Ther 8:150-155.
10. Jaganathan K S, et al. (2006), Vaccine, 24:4201-4211.
11. Sugai T, et al. (2005), Vaccine, 23:5450-5456.
12. Theeten H, et al. (2005), Vaccine, 23:1515-1521.
13. Caglar K, et al. (2005), APMIS, 113:256-263.
14. Flick-Smith H C, et al. (2002), Infect. Immun. 70:2022-2028.
15. Petrik M S, et al. (2007), Neuromolecular Med. 9:83-100.
16. Levesque P M, et al. (2006), Hum. Vaccin. 2:74-77.
17. Hedlund J, et al. (2002), Vaccine 20:164-169.
18. Sen G, et al. (2006), Infect. Immun. 74:2177-2186.
19. Sabirov A, Metzger D W. (2006), Vaccine, 24:5584-5592.
20. Pimenta F C, et al. (2006), Infect. Immun., 74:4939-4944.
21. Mullen G E D, et al. (2006), Vaccine, 24:2497-2505.
22. Langermans J A M, et al. (2005), Vaccine, 23:4935-4943.
23. Stewart V A, et al. (2006), Vaccine, 24:6483-6492.
24. Brando C, et al. (2006), Infect. Immun. Epub.
25. Rosado-Vallado M, et al. (2005), Vaccine, 23:5372-5379.
26. Kenney R T, et al. (1999), J. Immunol., 163:4481-4488.
27. Mendez S, et al. (2003), Infect. Immun., 71:5121-5129.
28. Vitetta E S, et al. (2006), Proc. Nat. Acad. Sci. (USA), 103:2268-2273.
29. Griffiths G D, et al. (1997), Vaccine, 15:1933-1939.
30. Kende M, et al. (2006), Vaccine, 24:2213-2221.
31. Eldridge J H, et al. (1991), Infect. Immun., 59:2978-2986.
32. Desai M P, et al. (2000), J. Microencapsul., 17:215-225.
33. Palese (2006), Emerg. Inf. Dis., 12 (1): 61-65.
34. Caughey, B. and Baron, G. S. (2006), Nature (443(19): 803-810
35. Aguzzi, A. and Heikenwalder, M. (2006), Nature Reviews/Microbiology, 4:765-775.
36. A. Aguzzi, F. L. et al. (2003), Br Med Bull 66: 141-159.
37. D. Peretz, et al (2001), Nature 412: 739-743.
38. M. Enari, et al. (2001), Proc Natl Acad Sci USA 98: 9295-9299.

39. Polymenidou M, et al. (2004), Proc Natl Acad Sci USA, 101(Suppl. 2): 14670-14676.
40. M. F. Koller, T. et al. (2002), J Neuroimmunol 132: 113-116.
41. E. M. Sigurdsson, et al. (2002), Am J Pathol 161: 13-17.
42. S. Gilch, F. et al. (2003), J Biol Chem 278: 18524-18531.
43. E. Hanan, O. et al. (2001), Biochem Biophys Res Commun 280: 115-120.
44. E. Hanan, et al. (2001), Cell Mol Neurobiol 21: 693-703.
45. L. Souan, et al. (2001), Eur J Immunol 31: 2338-2346.
46. M. Arbel, et al. (2003), J Neuroimmunol 144: 38-45.
47. A. Schwarz, et al. (2003), Neurosci Lett 350: 187-189.
48. M. B. Rosset, et al. (2004), J Immunol 172: 5168-5174.

What is claimed is:

1. A pharmaceutically acceptable preparation comprising a pharmaceutically acceptable carrier solution, an infectious pathogen or biological toxin antigen preparation of interest and an acellular adjuvant useful in enhancing immunogenicity of an infectious pathogen or biological toxin suitable for use in a vaccine, said acellular adjuvant comprising an acellular mammalian extracellular matrix material.

2. The pharmaceutically acceptable preparation of claim 1, wherein the vaccine is a vaccine for tetanus, influenza, rabies, viral hepatitis, diphtheria, anthrax, Streptococcus pneumonia infection, malaria, leismaniasis, ricin toxicosis, prions, or Staphylococcus enterotoxin B.

3. The pharmaceutically acceptable preparation of claim 1, wherein the vaccine is a vaccine for tetanus.

4. The pharmaceutically acceptable preparation of claim 1, wherein the acellular mammalian extracellular matrix material has been subject to a decellularization process.

5. The pharmaceutically acceptable preparation of claim 1 wherein the infectious pathogen or biological toxin comprises an inactivated preparation.

6. A composition suitable for use as an infectious pathogen or biological toxin vaccine comprising:
an immunogenic amount of an infectious pathogen antigen preparation of interest suitable for use in a vaccine; and
an infectious pathogen vaccine acellular adjuvant comprising an acellular mammalian extracellular matrix material diluted in a 1:10 ratio in a pharmaceutically acceptable carrier solution.

7. The composition of claim 6, wherein the infectious pathogen antigen preparation of interest is a tetanus toxoid.

8. A method for immunizing an animal against an infectious pathogen or biological toxin of interest comprising:
administering a pharmaceutically acceptable preparation to an animal, said pharmaceutically acceptable preparation comprising a pharmaceutically acceptable carrier solution, an infectious pathogen or biological toxin antigen preparation of interest and an acellular adjuvant suitable for use in a vaccine, said acellular adjuvant comprising an acellular mammalian extracellular matrix material; and
providing an immunized animal.

9. The method of claim 8, wherein the pharmaceutically acceptable preparation is a tetanus vaccine.

10. The method of claim 8, wherein the pharmaceutically acceptable preparation is a vaccine for tetanus, influenza, rabies, viral hepatitis, diphtheria, anthrax, Streptococcus pneumonia infection, malaria, leismaniasis, ricin toxicosis, prions, or Staphylococcus enterotoxin B.

11. A method for immunizing an animal against an infectious pathogen of interest comprising:
administering an immunogenic amount of a composition comprising an infectious pathogen antigen of interest suitable for use in a vaccine and a vaccine adjuvant, wherein the adjuvant comprises an acellular mammalian extracellular matrix.

12. The method of claim 11, wherein the infectious pathogen antigen of interest comprises a tetanus toxoid preparation.

13. The method of claim 11 wherein the infectious pathogen of interest is tetanus toxoid and the immunogenic amount of the composition comprises 0.03 μg to 0.05 μg of the tetanus toxoid.

14. The method of claim 11 wherein the acellular mammalian extracellular matrix material is diluted in a 1:10 ratio in a pharmaceutically acceptable carrier solution.

15. A pharmaceutically acceptable preparation comprising a pharmaceutically acceptable carrier solution, an infectious pathogen antigen preparation of interest and an acellular mammalian extracellular matrix material, wherein the acellular mammalian extracellular matrix material is diluted in a pharmaceutically acceptable carrier solution in a ratio of about 1:2 to about 1:20.

16. The pharmaceutically acceptable preparation of claim 1 wherein the acellular mammalian extracellular matrix is diluted in a 1:10 ratio in a pharmaceutically acceptable carrier solution.

* * * * *